United States Patent [19] [11] Patent Number: 6,054,614
Shum et al. [45] Date of Patent: Apr. 25, 2000

[54] PROCESS FOR THE PREPARATION OF TETRALONE IMINES FOR THE PREPARATION OF ACTIVE PHARMACEUTICAL COMPOUNDS

[75] Inventors: Sai P. Shum, Hightstown; Paul A. Odorisio, Leonia, both of N.J.; Stephen D. Pastor, Danbury, Conn.

[73] Assignee: Ciba Specialty Chemicals Corporation, Tarrytown, N.Y.

[21] Appl. No.: 09/065,272

[22] Filed: Apr. 23, 1998

[51] Int. Cl.⁷ .................................................. C07C 249/02
[52] U.S. Cl. .......................................... 564/270; 564/308
[58] Field of Search ..................................... 564/270, 308

[56] References Cited

U.S. PATENT DOCUMENTS 4,536,518  8/1985  Welch, Jr. et al. ..................... 564/308

*Primary Examiner*—Peter O'Sullivan
*Attorney, Agent, or Firm*—Luther A. R. Hall

[57] ABSTRACT

4-(3,4-Dichlorophenyl)-3,4-dihydro-2H-naphthalen-1-ylidene-methylamine and related analogs are prepared from α-tetralone by a facile three-step process. This compound is the required intermediate to prepare sertraline, (1S-cis)-4-(3,4-dichlorophenyl)-1,2,3,4-tetrahydro-N-methyl-1-naphthylamine. Sertraline has selective serotonin uptake inhibitor activity making it a valuable antidepressant pharmaceutical product.

16 Claims, No Drawings

PROCESS FOR THE PREPARATION OF TETRALONE IMINES FOR THE PREPARATION OF ACTIVE PHARMACEUTICAL COMPOUNDS

The instant invention pertains to a novel process for preparing 4-(phenyl, 3-chlorophenyl, 4-chlorophenyl or 3,4-dichlorophenyl)-3,4-dihydro-2H-naphthalen-1-ylidene-alkylamine from α-tetralone.

BACKGROUND OF THE INVENTION

Tetralones are known for being particularly useful as synthesis intermediates for preparing different serotonin pre-synaptic inhibitor compounds with antidepressant activity. This is described more precisely in U.S. Pat. Nos. 4,029,731 and 4,045,488 and European Patent No. 30,081. Until now, the 4-aryltetralones have been prepared using a method comprising five steps described by Johnson and Daub in Organic Reactions, Vol. VI, pages 1–73 and in European Patent No. 30,081. This method involves (a) the reaction of benzoyl chloride with an aromatic hydrocarbon in the presence of aluminum chloride to form a benzophenone; (b) condensation of said benzophenone under the conditions of the Stobbe reaction in the presence of a strong base, such as potassium tert-butoxide, with diethyl succinate; (c) decarboxylation of the product obtained using an aqueous hydrobromic acid solution to form a 4,4-diarylbutenoic acid; (d) hydrogenation of said acid on palladium/charcoal to form the corresponding 4,4-diarylbutanoic acid; and (e) cyclization of the butanoic acid into a 4-aryltetralone either directly by means of hydrofluoric acid or polyphosphoric acid, or, after transformation into the corresponding acid chloride using thionyl chloride, by the action of aluminum chloride under the conditions of the Friedel-Crafts reaction.

It is clear that this known method has many synthetic drawbacks. In fact, it takes an extended period to complete since it comprises five steps which each require a relatively long reaction time. Moreover, it uses expensive reagents such as potassium tert-butoxide and palladium on charcoal catalyst, or aggressive agents very dangerous to use such as hydrobromic acid, hydrofluoric acid and thionyl chloride. Furthermore, because of the large number of steps required, the overall yield of the tetralone is very low. In the best cases, the yield does not exceed 40% with respect to the starting benzoyl chloride.

A synthesis of the tetralone is described in U.S. Pat. No. 5,019,655 and by I. B. Repinskaya et al., Zhur. Org. Khim., 18, 870 (1982).

The instant process provides a method of going directly to the desired imine intermediate.

The preparation of N-methyl-1-naphthylamine by the palladium on carbon dehydrogenation of the imine formed by the reaction of tetralone with methylamine is not specifically described. The procedure is described in U.S. Pat. Nos. 3,219,702; 3,219,704 and 4,431,841.

The conversion of 4-(3,4-dichlorophenyl)-3,4-dihydro-2H-naphthalen-1-ylidene-methylamine to sertraline is described in U.S. Pat. No. 4,536,518 and by W. M. Welch et al., J. of Medinical Chem. 1984, 27, 1508. A procedure for the preparation of 4-(3,4-dichlorophenyl)-3,4-dihydro-2H-naphthalen-1-ylidene-methylamine which is outside the scope of this invention is described in U.S. Pat. No. 4,855,500.

DETAILED DISCLOSURE

The instant invention relates to a new process for preparing the pharmaceutical intermediate 4-(phenyl, 3-chlorophenyl, 4-chlorophenyl or 3,4-dichlorophenyl)-3,4-dihydro-2H-naphthalen-1-ylidene-alkylamine from N-alkyl-1-naphthylamine according to the following scheme:

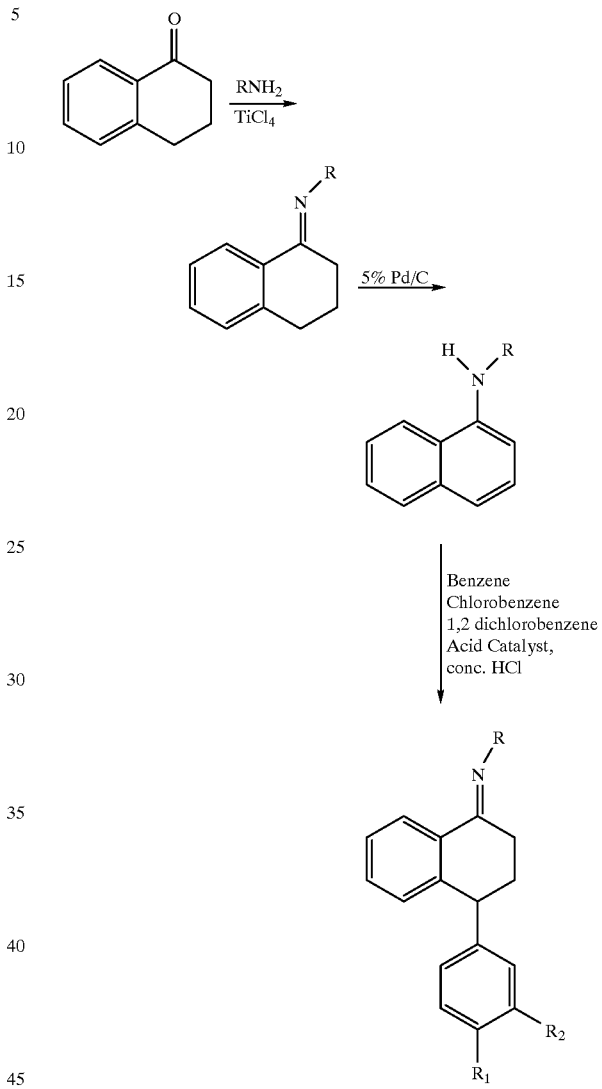

wherein

R is alkyl of 1 to 6 carbon atoms, and $R_1$ and $R_2$ are independently hydrogen or chloro.

Preferably R is methyl or ethyl, and $R_1$ and $R_2$ are both chloro. Most preferably, R is methyl.

More specifically, the instant process is a new method for preparing the pharmaceutical intermediate 4-(3,4-dichlorophenyl)-3,4-dihydro-2H-naphthalen-1-ylidene-methylamine from N-methyl-1-naphthylamine as seen below:

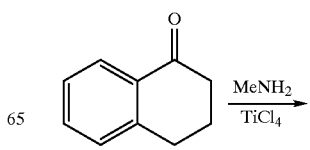

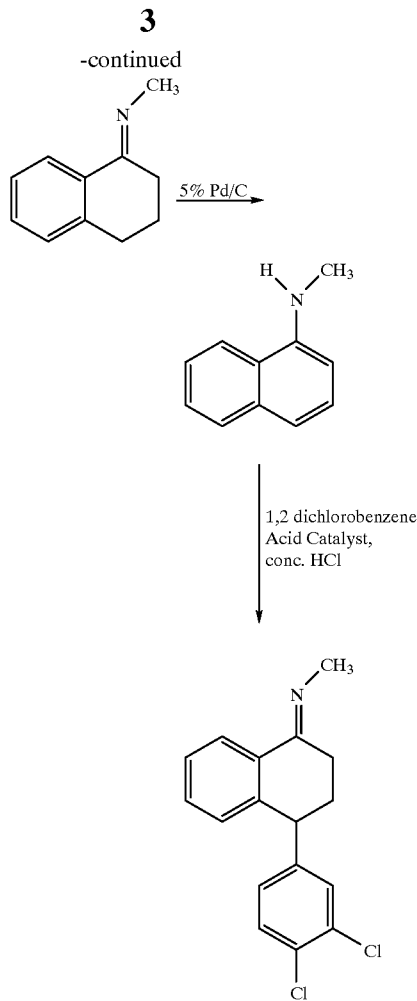

In the crucial third step of the above scheme, preferably the acid catalyst is aluminum bromide or aluminum chloride, most preferably aluminum chloride.

In said step, the amount of acid catalyst used is from one molar equivalent to six molar equivalents based on the N-alkyl-1-naphthylamine, preferably N-methyl-1-naphthylamine.

Most preferably, the third step is carried with aluminum bromide or aluminum chloride as acid catalyst in an amount 0.1 to 10 molar equivalents, preferably 4 to 8 molar equivalents, most preferably 5 to 7 molar equivalents, of acid catalyst based on N-alkyl-1-naphthylamine, preferably N-methyl-1-naphthylamine.

The examples given below are for illustrative purposes only and are not to be construed to limit the instant invention in any manner whatsoever.

EXAMPLE 1

Synthesis of N-Methyl-1-naphthylamine

Into a solution of 10 g (68 mmol) of α-tetralone in 140 mL of toluene is added 200 mL (400 mmol) of a 2.0 M tetrahydrofuran solution of methylamine at −5° C. to 0° C. After the addition is complete, the reaction mixture is cooled to −40° C. and 34.6 mL (34.6 mmol) of a 1 M solution of titanium tetrachloride in methylene chloride is added over a 15 minute period. After this addition is complete, the reaction mixture is allowed to warm to ambient temperature. After stirring at ambient temperature for 16 hours, the reaction mixture is filtered and the filtrate is concentrated to a crude oil. The crude oil is then dissolved in 150 mL of xylene and 200 mg of 5% palladium on charcoal catalyst is added. The reaction mixture is then heated to reflux for 16 hours. The palladium catalyst is then removed by filtration and the filtrate is concentrated to give 9 g of a crude oil which is purified by flash chromatography (silica gel, 2.5% ethyl acetate in hexane) to give 6 g of an oil in 60% yield.

EXAMPLE 2

Conversion of N-Methyl-1-naphthylamine to 4-(3,4-Dichlorophenyl)-3,4-dihydro-2H-naphthalen-1-ylidene-methylamine Into a suspension of 40 g (150 mmol) of aluminum bromide in 70 g of o-dichlorobenzene is added dropwise a solution of 4 g (25 mmol) of N-methyl-1-naphthylamine in 4 g of o-dichlorobenzene at ambient temperature. After the addition is completed in 15 minutes, 0.5 g (6 mmol) of a 48% solution of hydrobromic acid is added to the reaction mixture which is then heated to 100° C. After heating for two hours, only a trace amount of the N-methyl-1-naphthylamine is detected by thin layer chromatography analysis. Heating is continued for an additional two hours followed by cooling the reaction mixture to ambient temperature. The reaction mass is then added to 200 mL of chilled 2.5 N aqueous sodium hydroxide solution and stirred for 15 minutes. A total of 300 mL of ethyl acetate is used for extraction. All organic layers are combined and dried over anhydrous sodium sulfate and 3 g of activated carbon (DACRO® G-60, 100 mesh). After 15 minutes, the mixture is filtered and the light yellow filtrate is concentrated under vacuum to give 7.3 g of a crude solid (96% yield). The crude solid is recrystallized with ether to give 4.7 g (isolated yield 61.8%) of a white solid, melting at 142–144° C.

EXAMPLE 3

Conversion of N-Methyl-1-naphthylamine to 4-(3,4-Dichlorophenyl)-3,4-dihydro-2H-naphthalen-1-ylidene-methylamine Into a suspension of 20 g (150 mmol) of aluminum chloride in 70 g of o-dichlorobenzene is added dropwise a solution of 4 g (25 mmol) of N-methyl-1-naphthylamine in 4 g of o-dichlorobenzene at ambient temperature. After the addition is completed in 15 minutes, 0.6 g (6 mmol) of a 38% solution of hydrochloric acid is added to the reaction mixture which is then heated to 100° C. for 20 hours. The reaction mass is then added to 300 mL of chilled 2.5 N aqueous sodium hydroxide solution and stirred for 15 minutes. A total of 200 mL of ethyl acetate is used for extraction. All organic layers are combined and dried over anhydrous sodium sulfate and activated carbon (DACRO® G-60, 100 mesh). After 15 minutes, the mixture is filtered and the light yellow filtrate is concentrated under vacuum to give a crude solid. The crude solid is recrystallized with ether to give 4.3 g (isolated yield 56.6%) of a white solid, melting at 142–144° C.

EXAMPLE 4

Conversion of N-Ethyl-1-naphthylamine to 4-(3,4-Dichlorophenyl)-3,4-dihydro-2H-naphthalen-1-ylidene-ethylamine Into a suspension of 23.3 g (175 mmol) of aluminum chloride in 80 g of o-dichlorobenzene is added dropwise a solution of 5 g (29 mmol) of N-ethyl-1-naphthylamine in 5 g of o-dichlorobenzene at ambient temperature. After addition is completed in 15 minutes, 0.6 g (6 mmol) of a 38% solution of hydrochloric acid is added. The reaction mixture is then heated to 120° C. for 20 hours. The above-named product is detected by mass spectroscopy as the major product (m/z=317).

What is claimed is:

1. A process for the preparation of a compound of formula I

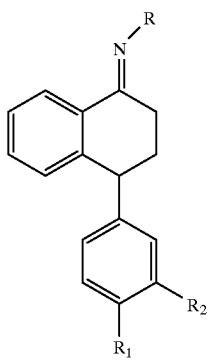

(I)

wherein
R is alkyl of 1 to 6 carbon atoms, and
$R_1$ and $R_2$ are independently hydrogen or chloro,
which comprises
reacting N-alkyl-1-naphthylamine of formula II

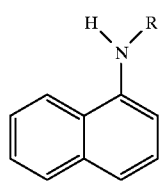

(II)

with a compound of formula III

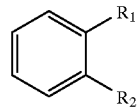

(III)

in the presence of an effective amount of an acid catalyst to form the compound of formula I.

2. A process according to claim 1 wherein R is methyl or ethyl, and $R_1$ and $R_2$ are both chloro.

3. A process according to claim 2 wherein R is methyl.

4. A process according to claim 1 wherein the acid catalyst is aluminum bromide or aluminum chloride.

5. A process according to claim 4 wherein the acid catalyst is aluminum chloride.

6. A process according to claim 1 wherein the acid catalyst is present in an amount from one molar equivalent to six molar equivalents based on the N-alkyl-1-naphthylamine.

7. A process according to claim 1 wherein the acid catalyst is present in an amount from 0.1 molar equivalent to 10 molar equivalents based on the N-alkyl-1-naphthylamine.

8. A process according to claim 7 wherein the acid catalyst is present in an amount from 4 molar equivalents to 8 molar equivalents based on the N-alkyl-1-naphthylamine.

9. A process according to claim 8 wherein the acid catalyst is present in an amount from 5 molar equivalents to 7 molar equivalents based on the N-alkyl-1-naphthylamine.

10. A process for the preparation of 4-(3,4-dichlorophenyl)-3,4-dihydro-2H-naphthalen-1-ylidene-methylamine of formula A

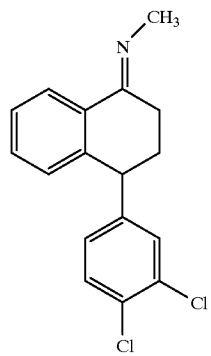

(A)

which comprises
reacting N-methyl-1-naphthylamine of the formula B

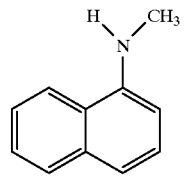

(B)

with o-dichlorobenzene of the formula C

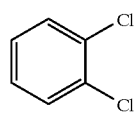

(C)

in the presence of an effective amount of an acid catalyst to form the compound of formula A.

11. A process according to claim 10 wherein the acid catalyst is aluminum bromide or aluminum chloride.

12. A process according to claim 11 wherein the acid catalyst is aluminum chloride.

13. A process according to claim 10 wherein the acid catalyst is present in an amount from one molar equivalent to six molar equivalents based on the N-methyl-1-naphthylamine.

14. A process according to claim 10 wherein the acid catalyst is present in an amount from 0.1 molar equivalent to 10 molar equivalents based on the N-methyl-1-naphthylamine.

15. A process according to claim 14 wherein the acid catalyst is present in an amount from 4 molar equivalents to 8 molar equivalents based on the N-methyl-1-naphthylamine.

16. A process according to claim 15 wherein the acid catalyst is present in an amount from 5 molar equivalents to 7 molar equivalents based on the N-methyl-1-naphthylamine.

* * * * *